(12) United States Patent
Alford et al.

(10) Patent No.: US 9,993,638 B2
(45) Date of Patent: Jun. 12, 2018

(54) DEVICES, SYSTEMS AND METHODS TO REDUCE COUPLING OF A SHIELD AND A CONDUCTOR WITHIN AN IMPLANTABLE MEDICAL LEAD

(71) Applicant: MEDTRONIC, INC., Minneapolis, MN (US)

(72) Inventors: Jamu K. Alford, Ham Lake, MN (US); Spencer M. Bondhus, Columbia Heights, MN (US); Michael Kalm, Spring Lake Park, MN (US); James M. Olsen, Plymouth, MN (US); Brian T. Stolz, Bloomington, MN (US); Richard T. Stone, Minneapolis, MN (US); Bryan D. Stem, Minneapolis, MN (US); John D. Welter, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days. days.

(21) Appl. No.: 14/568,547

(22) Filed: Dec. 12, 2014

(65) Prior Publication Data
US 2015/0170792 A1 Jun. 18, 2015

Related U.S. Application Data

(60) Provisional application No. 61/916,171, filed on Dec. 14, 2013.

(51) Int. Cl.
*A61N 1/05* (2006.01)
*A61N 1/08* (2006.01)

(52) U.S. Cl.
CPC ............. *A61N 1/05* (2013.01); *A61N 1/086* (2017.08)

(58) Field of Classification Search
USPC .................................................. 607/36, 113
See application file for complete search history.

(56) References Cited

U.S. PATENT DOCUMENTS

| 2,433,480 A | 12/1947 | Rendich |
| 2,487,038 A | 11/1949 | Jasper |

(Continued)

FOREIGN PATENT DOCUMENTS

| EP | 0617978 | 10/1994 |
| EP | 0624383 | 11/1994 |

(Continued)

OTHER PUBLICATIONS

PCT/US2004/042081: Search Report and Written Opinion.

(Continued)

*Primary Examiner* — Nicole F Johnson
(74) *Attorney, Agent, or Firm* — Withers & Keys, LLC

(57) ABSTRACT

Conductors within an implantable medical lead that carry stimulation signal signals are at least partially embedded within a lead body of the medical lead over at least a portion of the length of the conductors while being surrounded by a radio frequency (RF) shield. A space between the shield and the conductors is filled by the presence of the lead body material such that body fluids that infiltrate the lead over time cannot pool in the space between the shield and the conductors. The dielectric properties of the lead body are retained and the capacitive coupling between the shield and the conductors continues to be inhibited such that current induced on the shield is inhibited from being channeled onto the conductors. Heating at the electrodes of the medical lead is prevented from becoming excessive.

21 Claims, 7 Drawing Sheets

(56) References Cited

U.S. PATENT DOCUMENTS

| | | |
|---|---|---|
| 3,788,329 A | 1/1974 | Friedman |
| 3,842,485 A | 10/1974 | Bemert |
| 3,915,174 A | 10/1975 | Preston |
| 4,033,355 A | 7/1977 | Amundson |
| 4,038,990 A | 8/1977 | Thompson |
| 4,214,804 A | 7/1980 | Little |
| 4,220,813 A | 9/1980 | Kyle |
| 4,280,507 A | 7/1981 | Rosenberg |
| 4,320,763 A | 3/1982 | Money |
| 4,350,169 A | 9/1982 | Dutcher |
| 4,383,225 A | 5/1983 | Mayer |
| 4,403,824 A | 9/1983 | Scott |
| 4,441,498 A | 4/1984 | Nordling |
| 4,628,942 A | 12/1986 | Sweeney et al. |
| 4,683,895 A | 8/1987 | Pohndorf |
| 4,711,027 A | 12/1987 | Harris |
| 4,726,379 A | 2/1988 | Altman et al. |
| 4,852,585 A | 8/1989 | Heath |
| 4,906,241 A | 3/1990 | Noddin |
| 4,920,980 A | 5/1990 | Jackowski |
| 4,922,607 A | 5/1990 | Doan et al. |
| 4,934,380 A | 6/1990 | De Toledo |
| 4,947,866 A | 8/1990 | Lessar et al. |
| 4,951,672 A | 8/1990 | Buchwald et al. |
| 4,991,583 A | 2/1991 | Silvian |
| 5,003,992 A | 4/1991 | Holleman |
| 5,005,587 A | 4/1991 | Scott |
| 5,012,045 A | 4/1991 | Sato |
| 5,018,523 A | 5/1991 | Bach, Jr. et al. |
| 5,020,544 A | 6/1991 | Dahl et al. |
| 5,020,545 A | 6/1991 | Soukup |
| 5,036,862 A | 8/1991 | Pohndorf |
| 5,040,544 A | 8/1991 | Lessar et al. |
| 5,063,932 A | 11/1991 | Dahl et al. |
| 5,197,468 A | 3/1993 | Proctor et al. |
| 5,213,111 A | 5/1993 | Cook et al. |
| 5,217,010 A | 6/1993 | Tsitlik et al. |
| 5,231,078 A | 7/1993 | Riebman et al. |
| 5,243,996 A | 9/1993 | Hall |
| 5,246,438 A | 9/1993 | Langberg |
| 5,260,128 A | 11/1993 | Ishii et al. |
| 5,265,608 A | 11/1993 | Lee et al. |
| 5,265,623 A | 11/1993 | Kroll et al. |
| 5,271,417 A | 12/1993 | Swanson et al. |
| 5,308,664 A | 5/1994 | House et al. |
| 5,314,459 A | 5/1994 | Swanson et al. |
| 5,323,776 A | 6/1994 | Blakely et al. |
| 5,335,657 A | 8/1994 | Terry, Jr. et al. |
| 5,349,133 A | 9/1994 | Rogers |
| 5,360,441 A | 11/1994 | Otten |
| 5,366,496 A | 11/1994 | Dahl et al. |
| 5,370,644 A | 12/1994 | Langberg |
| 5,374,286 A | 12/1994 | Morris |
| 5,374,778 A | 12/1994 | Hashimoto et al. |
| 5,417,719 A | 5/1995 | Hull et al. |
| 5,456,705 A | 10/1995 | Morris |
| 5,458,629 A | 10/1995 | Baudino et al. |
| 5,458,631 A | 10/1995 | Xavier |
| 5,466,252 A | 11/1995 | Soukup et al. |
| 5,473,812 A | 12/1995 | Morris et al. |
| 5,476,496 A | 12/1995 | Strandberg et al. |
| 5,485,667 A | 1/1996 | Kleshinski |
| 5,500,013 A | 3/1996 | Buscemi et al. |
| 5,504,274 A | 4/1996 | McCabe et al. |
| 5,514,172 A | 5/1996 | Mueller |
| 5,515,848 A | 5/1996 | Corbett, III et al. |
| 5,523,534 A | 6/1996 | Meister et al. |
| 5,523,578 A | 6/1996 | Herskovic |
| 5,527,348 A | 6/1996 | Winkler |
| 5,534,018 A | 7/1996 | Wahlstrand |
| 5,552,565 A | 9/1996 | Cartier et al. |
| 5,571,157 A | 11/1996 | McConnell |
| 5,572,594 A | 11/1996 | DeVoe et al. |
| 5,591,218 A | 1/1997 | Jacobson |
| 5,594,304 A | 1/1997 | Graber |
| 5,606,981 A | 3/1997 | Tartacower et al. |
| 5,609,622 A | 3/1997 | Soukup et al. |
| 5,628,780 A | 5/1997 | Helland et al. |
| 5,629,622 A | 5/1997 | Scampini |
| 5,643,254 A | 7/1997 | Scheldrup et al. |
| 5,649,965 A | 7/1997 | Pons et al. |
| 5,662,697 A | 9/1997 | Li et al. |
| 5,676,659 A | 10/1997 | McGurk |
| 5,676,694 A | 10/1997 | Boser et al. |
| 5,683,435 A | 11/1997 | Truex et al. |
| 5,683,444 A | 11/1997 | Huntley et al. |
| 5,697,909 A | 12/1997 | Eggers et al. |
| 5,697,958 A | 12/1997 | Paul et al. |
| 5,702,437 A | 12/1997 | Baudino |
| 5,706,826 A | 1/1998 | Schwager |
| 5,722,998 A | 3/1998 | Prutchi et al. |
| 5,727,552 A | 3/1998 | Ryan |
| 5,751,539 A | 5/1998 | Stevenson et al. |
| 5,766,232 A | 6/1998 | Grevious et al. |
| 5,782,241 A | 7/1998 | Felblinger et al. |
| 5,795,341 A | 8/1998 | Samson |
| 5,807,258 A | 9/1998 | Cimochowski et al. |
| 5,814,076 A | 9/1998 | Brownlee |
| 5,827,997 A | 10/1998 | Chung et al. |
| 5,830,136 A | 11/1998 | Delonzor et al. |
| 5,842,966 A | 12/1998 | Markoll |
| 5,842,986 A | 12/1998 | Avrin et al. |
| 5,851,226 A | 12/1998 | Skubitz et al. |
| 5,897,584 A | 4/1999 | Herman |
| 5,905,627 A | 5/1999 | Brendel et al. |
| 5,927,345 A | 7/1999 | Samson |
| 5,931,861 A | 8/1999 | Werner et al. |
| 5,954,760 A | 9/1999 | Jarl |
| 5,964,705 A | 10/1999 | Truwit et al. |
| 5,968,087 A | 10/1999 | Hess |
| 5,970,429 A | 10/1999 | Martin |
| 5,942,966 A | 12/1999 | Markoll |
| 6,004,269 A | 12/1999 | Crowley |
| 6,016,447 A | 1/2000 | Juran et al. |
| 6,024,703 A | 2/2000 | Zanelli et al. |
| 6,032,063 A | 2/2000 | Hoar et al. |
| 6,033,408 A | 3/2000 | Gage et al. |
| 6,055,457 A | 4/2000 | Bonner |
| 6,101,417 A | 8/2000 | Vogel et al. |
| 6,103,037 A | 8/2000 | Wilson |
| 6,108,582 A | 8/2000 | Fischer, Sr. |
| 6,132,390 A | 10/2000 | Cookston et al. |
| 6,141,593 A | 10/2000 | Patag |
| 6,143,013 A | 11/2000 | Samson et al. |
| 6,152,746 A | 11/2000 | Brown |
| 6,156,029 A | 12/2000 | Mueller |
| 6,195,267 B1 | 2/2001 | MacDonald et al. |
| 6,198,807 B1 | 3/2001 | DeSena |
| 6,198,972 B1 | 3/2001 | Hartlaub et al. |
| 6,209,764 B1 | 4/2001 | Hartlaub et al. |
| 6,240,322 B1 | 5/2001 | Peterfeso |
| 6,258,071 B1 | 7/2001 | Brookes |
| 6,265,466 B1 | 7/2001 | Glatkowski |
| 6,269,148 B1 | 7/2001 | Jessop et al. |
| 6,284,971 B1 | 9/2001 | Atalar et al. |
| 6,302,740 B1 | 10/2001 | Holmstrom |
| 6,348,070 B1 | 2/2002 | Teissl et al. |
| 6,424,234 B1 | 7/2002 | Stevenson |
| 6,471,699 B1 | 10/2002 | Fleischman et al. |
| 6,488,704 B1 | 12/2002 | Connelly et al. |
| 6,494,916 B1 | 12/2002 | Babalola et al. |
| 6,501,991 B1 | 12/2002 | Honeck et al. |
| 6,503,648 B1 | 1/2003 | Wang |
| 6,506,972 B1 | 1/2003 | Wang |
| 6,529,774 B1 | 3/2003 | Greene |
| 6,538,191 B1 | 3/2003 | MacDonald |
| 6,583,361 B2 | 6/2003 | Clouet |
| 6,606,521 B2 | 8/2003 | Paspa et al. |
| 6,640,137 B2 | 10/2003 | MacDonald |
| 6,648,690 B2 | 11/2003 | Saito et al. |
| 6,660,116 B2 | 12/2003 | Wolf et al. |
| 6,671,544 B2 | 12/2003 | Baudino |
| 6,671,554 B2 | 12/2003 | Gibson et al. |
| 6,673,999 B1 | 1/2004 | Wang et al. |

(56) References Cited

U.S. PATENT DOCUMENTS

| | | |
|---|---|---|
| 6,675,033 B1 | 1/2004 | Lardo et al. |
| 6,689,835 B2 | 2/2004 | Amarasekera et al. |
| 6,695,761 B2 | 2/2004 | Oschman et al. |
| 6,708,051 B1 | 3/2004 | Durousseau |
| 6,711,440 B2 | 3/2004 | Deal et al. |
| 6,712,844 B2 | 3/2004 | Pacetti et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,735,471 B2 | 5/2004 | Hill et al. |
| 6,741,892 B1 | 5/2004 | Meadows et al. |
| 6,743,055 B1 | 6/2004 | Flynn |
| 6,750,055 B1 | 6/2004 | Connelly et al. |
| 6,757,566 B2 | 6/2004 | Weiner et al. |
| 6,760,628 B2 | 7/2004 | Weiner et al. |
| 6,763,268 B2 | 7/2004 | MacDonald et al. |
| 6,765,144 B1 | 7/2004 | Wang et al. |
| 6,768,053 B1 | 7/2004 | Wang et al. |
| 6,778,856 B2 | 8/2004 | Connelly et al. |
| 6,792,316 B2 | 9/2004 | Sass |
| 6,793,642 B2 | 9/2004 | Connelly et al. |
| 6,795,730 B2 | 9/2004 | Connelly et al. |
| 6,795,736 B2 | 9/2004 | Connelly et al. |
| 6,799,067 B2 | 9/2004 | Pacetti |
| 6,799,069 B2 | 9/2004 | Weiner et al. |
| 6,815,609 B1 | 11/2004 | Wang et al. |
| 6,819,954 B2 | 11/2004 | Connelly |
| 6,819,958 B2 | 11/2004 | Weiner et al. |
| 6,844,492 B1 | 1/2005 | Wang et al. |
| 6,845,259 B2 | 1/2005 | Pacetti et al. |
| 6,845,267 B2 | 1/2005 | Harrison et al. |
| 6,846,985 B2 | 1/2005 | Wang et al. |
| 6,850,805 B2 | 2/2005 | Connelly et al. |
| 6,852,091 B2 | 2/2005 | Edwards et al. |
| 6,863,653 B1 | 3/2005 | Zanelli et al. |
| 6,864,418 B2 | 3/2005 | Wang et al. |
| 6,869,683 B2 | 3/2005 | Sakurai et al. |
| 6,871,091 B2 | 3/2005 | Wilkinson et al. |
| 6,872,882 B2 | 3/2005 | Fritz |
| 6,875,180 B2 | 4/2005 | Weiner et al. |
| 6,879,861 B2 | 4/2005 | Benz et al. |
| 6,882,519 B2 | 4/2005 | Uzawa et al. |
| 6,895,280 B2 | 5/2005 | Meadows et al. |
| 6,901,287 B2 | 5/2005 | Davis et al. |
| 6,901,290 B2 | 5/2005 | Foster et al. |
| 6,906,256 B1 | 6/2005 | Wang |
| 6,920,361 B2 | 7/2005 | Williams |
| 6,922,590 B1 | 7/2005 | Whitehurst |
| 6,925,328 B2 | 8/2005 | Foster et al. |
| 6,930,242 B1 | 8/2005 | Helfer |
| 6,937,906 B2 | 8/2005 | Terry et al. |
| 6,944,489 B2 | 9/2005 | Zeiljemaker et al. |
| 6,949,929 B2 | 9/2005 | Gray et al. |
| 6,954,674 B2 | 10/2005 | Connelly |
| 6,968,235 B2 | 11/2005 | Belden et al. |
| 6,968,236 B2 | 11/2005 | Hagele |
| 6,971,391 B1 | 12/2005 | Wang et al. |
| 6,980,865 B1 | 12/2005 | Wang et al. |
| 6,982,378 B2 | 1/2006 | Dickson |
| 6,985,775 B2 | 1/2006 | Reinke et al. |
| 6,993,387 B2 | 1/2006 | Connelly et al. |
| 6,999,818 B2 | 2/2006 | Stevenson et al. |
| 6,999,821 B2 | 2/2006 | Jenney et al. |
| 7,001,369 B2 | 2/2006 | Griffin et al. |
| 7,013,174 B2 | 3/2006 | Connelly et al. |
| 7,013,180 B2 | 3/2006 | Villaseca et al. |
| 7,015,392 B1 | 3/2006 | Dickenson |
| 7,015,393 B2 | 3/2006 | Weiner |
| 7,047,084 B2 | 5/2006 | Erickson |
| 7,050,855 B2 | 5/2006 | Zeijlemaker et al. |
| 7,058,192 B2 | 6/2006 | Muller et al. |
| 7,076,283 B2 | 7/2006 | Cho et al. |
| 7,076,302 B2 | 7/2006 | Scheiner |
| 7,082,328 B2 | 7/2006 | Funke |
| 7,082,337 B2 | 7/2006 | Sommer et al. |
| 7,103,413 B2 | 9/2006 | Swanson |
| 7,113,827 B2 | 9/2006 | Silvestri |
| 7,115,134 B2 | 10/2006 | Chambers |
| 7,118,693 B2 | 10/2006 | Glatkowski et al. |
| 7,123,013 B2 | 10/2006 | Gray |
| 7,125,409 B2 | 10/2006 | Truckai et al. |
| 7,162,302 B2 | 1/2007 | Wang et al. |
| 7,174,219 B2 | 2/2007 | Wahlstrand et al. |
| 7,187,980 B2 | 3/2007 | Osypka et al. |
| 7,233,825 B2 | 6/2007 | Jorgenson et al. |
| 7,257,449 B2 | 8/2007 | Bodner |
| 7,282,260 B2 | 10/2007 | LeGrande et al. |
| 7,286,871 B2 | 10/2007 | Cohen |
| 7,286,882 B2 | 10/2007 | Cole |
| 7,292,894 B2 | 11/2007 | Belden |
| 7,294,785 B2 | 11/2007 | Uutela et al. |
| 7,319,901 B2 | 1/2008 | Dublin |
| 7,363,090 B2 | 4/2008 | Halperin |
| 7,389,148 B1 | 6/2008 | Morgan |
| 7,540,865 B2 | 6/2009 | Griffin et al. |
| 7,548,788 B2 | 6/2009 | Chinn et al. |
| 7,591,831 B2 | 9/2009 | Parsonage et al. |
| 7,674,972 B2 | 3/2010 | Gladd et al. |
| 7,711,436 B2 | 5/2010 | Stone |
| 7,729,777 B2 | 6/2010 | Gray et al. |
| 7,738,942 B2 | 6/2010 | Weiner |
| 7,813,811 B2 | 10/2010 | Wingeier et al. |
| 7,819,826 B2 | 10/2010 | Diederich et al. |
| 7,822,484 B1 | 10/2010 | Zhao et al. |
| 7,828,833 B2 | 11/2010 | Haverkost |
| 7,844,343 B2 | 11/2010 | Wahlstrand |
| 7,844,344 B2 | 11/2010 | Wahlstrand |
| 7,853,332 B2 | 12/2010 | Olsen |
| 7,877,150 B2 | 1/2011 | Hoegh |
| 7,904,178 B2 | 3/2011 | Williams |
| 7,917,213 B2 | 3/2011 | Bulkes |
| 7,933,652 B2 | 4/2011 | Phillips |
| 8,007,440 B2 | 8/2011 | Magnin et al. |
| 8,027,736 B2 | 9/2011 | Wahlstrand |
| 8,036,756 B2 | 10/2011 | Swoyer et al. |
| 8,048,060 B2 | 11/2011 | Griffin et al. |
| 8,055,351 B2 | 11/2011 | Atalar et al. |
| 8,106,657 B2 | 1/2012 | Sakellariou et al. |
| 8,170,691 B2 | 5/2012 | Eckerdal |
| 8,202,259 B2 | 6/2012 | Evans et al. |
| 8,246,643 B2 | 8/2012 | Nita |
| 8,275,464 B2 | 9/2012 | Li et al. |
| 8,280,526 B2 | 10/2012 | Wahlstrand |
| 8,483,842 B2 | 7/2013 | Alexander et al. |
| 8,620,455 B2 | 12/2013 | Alexander et al. |
| 8,676,340 B2 | 3/2014 | Wahlstrand |
| 8,744,598 B2 | 6/2014 | Alexander et al. |
| 8,788,061 B2 | 7/2014 | Mehdizadeth |
| 8,805,534 B2 | 8/2014 | Olsen |
| 8,903,504 B2 | 12/2014 | Hegland |
| 9,002,474 B2 | 4/2015 | Olsen |
| 9,037,263 B2 | 5/2015 | Marshall |
| 9,044,593 B2 | 6/2015 | Li |
| 2001/0044646 A1 | 11/2001 | Marshall et al. |
| 2002/0032468 A1 | 3/2002 | Hill |
| 2002/0038135 A1 | 3/2002 | Connelly et al. |
| 2002/0058978 A1 | 5/2002 | Sass |
| 2002/0183438 A1 | 5/2002 | Amarasekera et al. |
| 2002/0082673 A1 | 6/2002 | Benz et al. |
| 2002/0106918 A1 | 8/2002 | Saito et al. |
| 2002/0111659 A1 | 8/2002 | Davis et al. |
| 2002/0111663 A1 | 8/2002 | Dahl et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |

(56) References Cited

U.S. PATENT DOCUMENTS

| | | |
|---|---|---|
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0143377 A1 | 10/2002 | Wessman et al. |
| 2002/0183740 A1 | 12/2002 | Edwards et al. |
| 2002/0183822 A1 | 12/2002 | Bodner |
| 2002/0188345 A1 | 12/2002 | Pacetti |
| 2003/0009207 A1 | 1/2003 | Paspa et al. |
| 2003/0014080 A1 | 1/2003 | Baudino |
| 2003/0036776 A1 | 2/2003 | Foster et al. |
| 2003/0044623 A1 | 3/2003 | Sakurai et al. |
| 2003/0045920 A1 | 3/2003 | Belden et al. |
| 2003/0060732 A1 | 3/2003 | Jacobsen et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0093107 A1 | 5/2003 | Parsonage et al. |
| 2003/0109901 A1 | 6/2003 | Greatbatch |
| 2003/0117787 A1 | 6/2003 | Nakauchi |
| 2003/0120148 A1 | 6/2003 | Pacetti |
| 2003/0120197 A1 | 6/2003 | Kaneko et al. |
| 2003/0135114 A1 | 7/2003 | Pacetti et al. |
| 2003/0139794 A1 | 7/2003 | Jenney et al. |
| 2003/0139806 A1 | 7/2003 | Haverkost et al. |
| 2003/0140931 A1 | 7/2003 | Zeijlemaker |
| 2003/0144704 A1 | 7/2003 | Terry |
| 2003/0144705 A1 | 7/2003 | Funke |
| 2003/0144716 A1 | 7/2003 | Reinke et al. |
| 2003/0144717 A1 | 7/2003 | Hegele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0167052 A1 | 9/2003 | Lee et al. |
| 2003/0204217 A1 | 10/2003 | Greatbatch |
| 2003/0225331 A1 | 12/2003 | Diederich et al. |
| 2004/0020674 A1 | 2/2004 | McFadden et al. |
| 2004/0024442 A1 | 2/2004 | Sowinski et al. |
| 2004/0028859 A1 | 2/2004 | LeGrande et al. |
| 2004/0039434 A1* | 2/2004 | Schrom ............... A61N 1/0551 607/118 |
| 2004/0068307 A1 | 4/2004 | Goble |
| 2004/0071949 A1 | 4/2004 | Glatkowski et al. |
| 2004/0088012 A1 | 5/2004 | Kroll et al. |
| 2004/0106958 A1 | 6/2004 | Mathis et al. |
| 2004/0162600 A1 | 8/2004 | Williams |
| 2004/0167443 A1 | 8/2004 | Shireman et al. |
| 2004/0173368 A1 | 9/2004 | Dickson |
| 2004/0199069 A1 | 10/2004 | Connelly et al. |
| 2004/0220549 A1 | 11/2004 | Dittman et al. |
| 2004/0249428 A1 | 12/2004 | Wang et al. |
| 2004/0251042 A1 | 12/2004 | Weiner et al. |
| 2004/0263172 A1 | 12/2004 | Gray et al. |
| 2004/0263173 A1 | 12/2004 | Gray |
| 2004/0263174 A1 | 12/2004 | Gray et al. |
| 2004/0267328 A1 | 12/2004 | Duffin |
| 2005/0065587 A1 | 3/2005 | Gryzwa |
| 2005/0070972 A1 | 3/2005 | Wahlstrand |
| 2005/0080471 A1 | 4/2005 | Chitre et al. |
| 2005/0113876 A1 | 5/2005 | Weiner |
| 2005/0115624 A1 | 6/2005 | Walak |
| 2005/0137664 A1 | 6/2005 | Sommer et al. |
| 2005/0145307 A1 | 7/2005 | Shireman et al. |
| 2005/0159661 A1 | 7/2005 | Connelly et al. |
| 2005/0182471 A1 | 8/2005 | Wang |
| 2005/0222642 A1 | 10/2005 | Przybyszewski |
| 2005/0222647 A1 | 10/2005 | Wahlstrand |
| 2005/0222656 A1 | 10/2005 | Wahlstrand |
| 2005/0222657 A1 | 10/2005 | Wahlstrand |
| 2005/0222658 A1 | 10/2005 | Hoegh et al. |
| 2005/0222659 A1 | 10/2005 | Olsen |
| 2006/0030918 A1 | 2/2006 | Chinn et al. |
| 2006/0036306 A1 | 2/2006 | Heist et al. |
| 2006/0079926 A1 | 4/2006 | Desai et al. |
| 2006/0089680 A1 | 4/2006 | Bruchmann et al. |
| 2006/0095078 A1 | 5/2006 | Tronnes |
| 2006/0135962 A1 | 6/2006 | Kick et al. |
| 2006/0155270 A1 | 7/2006 | Hancock |
| 2006/0167522 A1 | 7/2006 | Malinowski |
| 2006/0167527 A1 | 7/2006 | Malinowski |
| 2006/0200218 A1 | 9/2006 | Wahlstrand |
| 2006/0224207 A1 | 10/2006 | Dublin |
| 2006/0247747 A1 | 11/2006 | Olsen |
| 2006/0247748 A1 | 11/2006 | Wahlstrand |
| 2007/0021811 A1 | 1/2007 | D'Aquanni et al. |
| 2007/0106332 A1 | 5/2007 | Denker |
| 2007/0123805 A1 | 5/2007 | Shireman et al. |
| 2007/0129779 A1 | 6/2007 | Ayre et al. |
| 2007/0168008 A1 | 7/2007 | Olsen |
| 2007/0185556 A1 | 8/2007 | Williams |
| 2007/0208383 A1 | 9/2007 | Williams |
| 2007/0293924 A1 | 12/2007 | Belden et al. |
| 2008/0033497 A1 | 2/2008 | Bulkes |
| 2008/0039709 A1 | 2/2008 | Karmarkar |
| 2008/0058715 A1 | 3/2008 | Houser et al. |
| 2008/0154326 A1 | 6/2008 | Clyne |
| 2008/0183263 A1 | 7/2008 | Alexander |
| 2008/0195186 A1 | 8/2008 | Li |
| 2008/0195187 A1 | 8/2008 | Li |
| 2008/0215008 A1 | 9/2008 | Nance et al. |
| 2008/0242944 A1 | 10/2008 | Sharma |
| 2008/0243081 A1 | 10/2008 | Nance et al. |
| 2008/0243218 A1 | 10/2008 | Bottomley |
| 2008/0262582 A1 | 10/2008 | Alexander |
| 2008/0262584 A1 | 10/2008 | Bottomley |
| 2008/0269863 A1 | 10/2008 | Alexander |
| 2008/0287804 A1 | 11/2008 | Nita |
| 2009/0118610 A1* | 5/2009 | Karmarkar ........... A61B 5/0476 600/420 |
| 2009/0204192 A1 | 8/2009 | Carlton |
| 2009/0221970 A1 | 9/2009 | Spinoza |
| 2009/0228074 A1 | 9/2009 | Edgell et al. |
| 2009/0234402 A1 | 9/2009 | Marshall |
| 2009/0240235 A1 | 9/2009 | Murata |
| 2009/0259272 A1 | 10/2009 | Reddy |
| 2009/0270956 A1 | 10/2009 | Vase |
| 2009/0287189 A1 | 11/2009 | Suwito |
| 2010/0036466 A1* | 2/2010 | Min ........................ A61N 1/05 607/116 |
| 2010/0069743 A1 | 3/2010 | Sheetz et al. |
| 2010/0100164 A1 | 4/2010 | Johnson et al. |
| 2010/0137957 A1 | 6/2010 | Eckerdal |
| 2010/0145426 A1 | 6/2010 | Stone |
| 2010/0198327 A1 | 8/2010 | Helland |
| 2010/0256528 A1 | 10/2010 | Lippert et al. |
| 2010/0256604 A1 | 10/2010 | Lippert et al. |
| 2010/0268310 A1 | 10/2010 | Bonde et al. |
| 2010/0331938 A1 | 12/2010 | Sommer |
| 2011/0015713 A1 | 1/2011 | Min |
| 2011/0034983 A1 | 2/2011 | Min |
| 2011/0071599 A1 | 3/2011 | Olsen |
| 2011/0071604 A1 | 3/2011 | Wahlstrand |
| 2011/0071605 A1 | 3/2011 | Wahlstrand |
| 2011/0112615 A1 | 5/2011 | Hoegh et al. |
| 2011/0230943 A1 | 9/2011 | Johnson et al. |
| 2011/0251487 A1 | 10/2011 | Magnin et al. |
| 2011/0276116 A1* | 11/2011 | Maxfield ............. A61N 1/0563 607/116 |
| 2011/0319905 A1 | 12/2011 | Palme et al. |
| 2012/0010689 A1 | 1/2012 | Wahlstrand |
| 2012/0035616 A1 | 2/2012 | Olsen et al. |
| 2012/0035694 A1 | 2/2012 | Olsen |
| 2012/0035695 A1 | 2/2012 | Olsen et al. |
| 2012/0035696 A1 | 2/2012 | Kern |
| 2012/0035697 A1 | 2/2012 | Stone |
| 2012/0035951 A1 | 2/2012 | Goetz |
| 2012/0041528 A1 | 2/2012 | Mehdizadeh et al. |
| 2012/0041529 A1 | 2/2012 | Olsen |
| 2012/0046722 A1 | 2/2012 | Olsen et al. |

(56) References Cited

U.S. PATENT DOCUMENTS

| | | | |
|---|---|---|---|
| 2012/0635696 | | 2/2012 | Kern |
| 2012/0053664 | A1 | 3/2012 | Hegland |
| 2012/0059467 | A1 | 3/2012 | Drew |
| 2012/0130461 | A1 | 5/2012 | Olsen |
| 2012/0330383 | A1 | 12/2012 | Wahlstrand |
| 2013/0296991 | A1 | 11/2013 | Alexander et al. |
| 2014/0107746 | A1 | 4/2014 | Alexander et al. |
| 2014/0200643 | A1 | 7/2014 | Wahlstrand |
| 2014/0288626 | A1 | 9/2014 | Alexander et al. |
| 2014/0345132 | A1 | 11/2014 | Mehdizadeh et al. |
| 2014/0350654 | A1 | 11/2014 | Olsen et al. |
| 2015/0082618 | A1 | 3/2015 | Hegland |

FOREIGN PATENT DOCUMENTS

| | | |
|---|---|---|
| EP | 0713714 | 5/1996 |
| EP | 0760196 | 3/1997 |
| EP | 0920239 | 6/1999 |
| EP | 1273922 | 1/2003 |
| EP | 1424095 | 6/2004 |
| EP | 1466576 | 10/2004 |
| EP | 1625875 | 2/2006 |
| EP | 1632265 | 3/2006 |
| EP | 1935449 | 6/2008 |
| GB | 2429154 | 2/2007 |
| JP | 07/255863 | 10/1995 |
| JP | 11/086641 | 3/1999 |
| WO | WO95/032673 | 12/1995 |
| WO | WO96/016694 | 6/1996 |
| WO | WO96/028951 | 9/1996 |
| WO | WO97/041923 | 11/1997 |
| WO | WO98/048896 | 11/1998 |
| WO | WO99/010035 | 3/1999 |
| WO | WO99/019020 | 4/1999 |
| WO | WO99/060370 | 11/1999 |
| WO | WO00/027279 | 5/2000 |
| WO | WO01/080940 | 11/2001 |
| WO | WO02/000292 | 1/2002 |
| WO | WO02/083236 | 10/2002 |
| WO | WO03/037429 | 5/2003 |
| WO | WO03/061755 | 7/2003 |
| WO | WO03/063946 | 8/2003 |
| WO | WO03/063948 | 8/2003 |
| WO | WO03/063952 | 8/2003 |
| WO | WO03/063953 | 8/2003 |
| WO | WO03/063954 | 8/2003 |
| WO | WO03/063955 | 8/2003 |
| WO | WO03/063956 | 8/2003 |
| WO | WO03/063957 | 8/2003 |
| WO | WO03/075797 | 9/2003 |
| WO | WO03/092326 | 11/2003 |
| WO | WO03/095022 | 11/2003 |
| WO | WO04/012809 | 2/2004 |
| WO | WO04/052448 | 6/2004 |
| WO | WO04/073040 | 8/2004 |
| WO | WO05/030322 | 4/2005 |
| WO | WO05/032654 | 4/2005 |
| WO | WO05/102444 | 11/2005 |
| WO | WO05/102445 | 11/2005 |
| WO | WO05/102446 | 11/2005 |
| WO | WO05/102447 | 11/2005 |
| WO | WO06/031317 | 3/2006 |
| WO | WO06/093685 | 9/2006 |
| WO | WO06/093686 | 9/2006 |
| WO | WO06/118640 | 11/2006 |
| WO | WO06/118641 | 11/2006 |
| WO | WO07/047966 | 4/2007 |
| WO | WO07/124273 | 11/2007 |
| WO | WO07/126657 | 11/2007 |
| WO | WO07/149757 | 12/2007 |
| WO | WO08/088568 | 7/2008 |
| WO | WO08/100839 | 8/2008 |
| WO | WO08/100840 | 8/2008 |
| WO | WO08/111986 | 9/2008 |
| WO | WO08/130409 | 10/2008 |
| WO | WO08/134196 | 11/2008 |
| WO | WO08/140376 | 11/2008 |
| WO | WO09/011440 | 9/2009 |
| WO | WO09/134901 | 11/2009 |
| WO | WO10/062988 | 6/2010 |
| WO | WO10/126871 | 11/2010 |
| WO | WO10/126877 | 11/2010 |
| WO | WO10/126884 | 11/2010 |
| WO | WO10/126887 | 11/2010 |
| WO | WO10/126935 | 11/2010 |
| WO | WO10/126939 | 11/2010 |
| WO | WO10/126943 | 11/2010 |
| WO | WO10/126946 | 11/2010 |
| WO | WO10/126949 | 11/2010 |
| WO | WO10/126975 | 11/2010 |
| WO | WO10/135440 | 11/2010 |
| WO | WO11/019416 | 2/2011 |
| WO | WO12/103419 | 8/2012 |
| WO | WO13/158189 | 10/2013 |

OTHER PUBLICATIONS

PCT/US2005/000322: Search Report and Written Opinion.
PCT/US2008/053540: Search Report and Written Opinion.
PCT/US2008/053541: Search Report and Written Opinion.
PCT/US2008/059358: Search Report and Written Opinion.
PCT/US2009/036461: Search Report and Written Opinion.
PCT/US2010/032516: Search Report and Written Opinion.
PCT/US2010/032526: Search Report and Written Opinion.
PCT/US2010/032543: Search Report and Written Opinion.
PCT/US2010/032560: Search Report and Written Opinion.
PCT/US2010/032567: Search Report and Written Opinion.
PCT/US2010/032666: Search Report and Written Opinion.
PCT/US2010/032671: Search Report and Written Opinion.
PCT/US2010/032675: Search Report and Written Opinion.
PCT/US2010/032682: Search Report and Written Opinion.
PCT/US2010/032719: Search Report and Written Opinion.
PCT/US2013/023637: Search Report and Written Opinion.
Baker et al., "Evaluation of Specific Absorption Rates as a Dosimeter of MRI-Related Implant Heating", Journal of Magnetic Resonance Imaging 20:315-320 (2004).
Baker, K., et al., "Neurostimulation Systems: Assessment of Magnetic Field Interactions Associated with 1.5 and 3-Tesla MR Systems", J. Magn. Reson. Imaging, Jan. 2005, 21(1);72-7.
Chung, D.D.L., "Carbon Fiber Composites", 1994, chapter 1, p. 8, table 1.2, Elsevier, ISBN: 978-0-7506-9169-7.
Chung, D.D.L., Comparison of Submicron-Diameter Carbon Filaments and Conventional Carbon Fibers as Fillers in Composite Materials, Carbon 39 (2001) pp. 1119-1125, Elsevier Science Ltd.
Chung, D.D.L., Electromagnetic Interference Shielding Effectiveness of Carbon Materials, Carbon 29 (2001) pp. 279-285, Elsevier Science Ltd.
Engdahl, Tomi, "Ground Loop Basics." Web Jan. 4, 2009, ePanorama.net www.epanorama.net/documents/goundloop/basics.html 28052.00 U.S. Appl. No. 11/739,787.
Finelli, D., et al., "MRI Imaging-Related Heating of Deep Brain Stimulation Electrodes: In Vitro Study", AJNR AM. J. Neuroadiol 23:1, Nov./Dec. 2002.
Jou, W.S. "A Novel Structure of Woven Continuous-Carbon Fiber Composites with High Electromagnetic Shielding", Journal of Electronic Materials, vol. 33, No. 3, Mar. 1, 2004, pp. 162-170(9), Minerals, Metals and Materials Society, http://findarticles.com/p/articles/mi_qu3776/is_200403/ai_n9405_582/print.
Kolin, et al., "An Electromagnetic Catheter Flow Meter for Determination of Blood Flow in Major Arteries," Department of Biophysics, Physiology, and Radiology, University of California School of Medicine (Los Angeles) Jan. 19, 1988, Proc. N.A.S. vol. 59, pp. 808-815.
Kolin, et al., "An Electromagnetic Intravascular Blood-Flow Sensor", Department of Biophysics, University of California School of Medicine (Los Angeles), Mar. 20, 1967, Proc. N.A.S., vol. 57, pp. 1331-1337.
Kolin, et al., "Miniaturization of the Electromagnetic Blood Flow Meter and Its Use for the Recording of Circulatory Responses of

(56) References Cited

OTHER PUBLICATIONS

Conscious Animals to Sensory Stimuli", Department of Biophysics, University of California at Los Angeles, Aug. 1959, Proc. N.A.S. vol. 45(8), pp. 1312-1321.

Medtronic Activa Product Family and Procedure Solution Brochure, Medtronic, Inc, 2001.

Medtronic Neurostimulation Systems Brochure, Medtronic, Inc., 2002.

Quick et al., "Endourethral MRI", Magnetic Resonance in Medicine, 45:138-146, 2001.

Rezai, A., et al., "Neurostimulation System Used for Deep Brain Stimulation (DBS): MR Safety Issues and Implications of Failing to Follow Safety Recommendations" Investigative Radiology, May 2004, vol. 39, Issue 5, pp. 300-303.

Rezai, A., et al., "Neurostimulation Systems for Deep Brain Stimulation In Vitro Evaluation of Magnetic Resonance Imaging-Related Healing at 1.5 Tesla", Journal of Magnetic Reson. Imaging 2002; 15:241-50.

\* cited by examiner

DEVICES, SYSTEMS AND METHODS TO REDUCE COUPLING OF A SHIELD AND A CONDUCTOR WITHIN AN IMPLANTABLE MEDICAL LEAD

TECHNICAL FIELD

Embodiments are related to implantable medical leads having shields for blocking electromagnetic energy from coupling onto conductors. More specifically, embodiments are related to reducing the coupling of the shield to the conductor(s) within the implantable medical device.

BACKGROUND

Implantable medical leads are used to provide electrical stimulation from a pulse generator to a target site within a body of a patient. The lead includes electrical conductors that extend from a proximal end that is coupled to the pulse generator to a distal end. The conductors carry stimulation signals to electrodes on the distal end that are positioned at the target site and deliver the stimulation signals to the tissue.

The presence of the lead presents a risk if the patient undergoes a magnetic resonance imaging (MRI) scan. Radio frequency (RF) energy that is present during the MRI scan may couple to the conductor(s) within the lead which results in electrical current on the conductor that can cause potentially dangerous heating of tissue nearby the electrode. This is especially problematic for neurostimulation leads where the electrode is placed in very sensitive neurological tissue such as within the brain or spine.

Various techniques have been devised to try to lessen the current being induced onto the conductor by the RF energy to thereby lessen the amount of heating at the electrode. One technique is to include a conductive RF shield that surrounds the conductor. The RF energy is largely blocked from reaching the conductor and the induced current and tissue heating are reduced.

The conductor is typically located in a lumen of the lead while the shield may be present outside of the lumen, typically in a polymer jacket. Over time, body fluids infiltrate the polymer jacket of the lead and reach the lumen which fills with the fluid. Thus, a significant amount of body fluid could be present between the shield and the conductor being shielded. Because the body fluid presents a high dielectric constant, capacitive coupling may occur to some degree between the shield and the conductor which could result in some of the RF energy being transferred to the conductor.

SUMMARY

Embodiments address issues such as these and others by providing a lead where at least a portion of the diameter of the conductor is embedded within a lead body that contains the shield such that a space between a shield and the conductor is entirely filled with the lead body material. This eliminates body fluid from being pooled between the shield and the conductor and thereby lessens the capacitive coupling that occurs to thereby limit increases in heating over time.

Embodiments provide a method of providing a medical lead that includes providing a conductor having a diameter and providing a radio frequency (RF) shield that surrounds the conductor such that a space exists between the shield and the conductor. The method further involves providing a lead body with a lumen where the lead body encapsulates the shield and surrounds the conductor with a portion of the conductor diameter being embedded within the lead body and the lead body filling the space. The method further involves providing an electrode attached to the lead body and electrically coupled to the conductor.

Embodiments provide a method of providing a medical lead. The method involves forming an inner lead body layer of a lead body about a conductor to embed a portion of a diameter of the conductor within the inner lead body layer and positioning a radio frequency (RF) shield about the lead body inner layer. The method further involves forming an outer lead body layer of the lead body about the shield and the inner lead body layer to encapsulate the shield and to bond with the inner lead body layer and providing an electrode attached to the lead body and electrically coupled to the conductor.

Embodiments provide an implantable medical lead that includes a conductor having a diameter and a radio frequency (RF) shield that surrounds the conductor such that a space exists between the shield and the conductor. The lead includes a lead body with a lumen, the lead body encapsulating the shield and surrounding the conductor with a portion of the conductor diameter being embedded within the lead body and the lead body filling the space. The lead further includes an electrode attached to the lead body and electrically coupled to the conductor.

Embodiments provide an implantable medical system that includes a pulse generator and a medical lead. The medical lead includes a conductor having a diameter, the conductor being electrically coupled to the pulse generator. The medical lead includes a radio frequency (RF) shield that surrounds the conductor such that a space exists between the shield and the conductor. The lead includes a lead body with a lumen and the lead body encapsulates the shield and surrounds the conductor with a portion of the conductor diameter being embedded within the lead body and with the lead body filling the space. The lead further includes an electrode attached to the lead body and electrically coupled to the conductor.

Embodiments provide an implantable medical lead that includes a conductor having a diameter and a radio frequency (RF) shield that surrounds the conductor such that a space exists between the shield and the conductor. The lead includes a lead body with a lumen, the lead body encapsulating the shield and surrounding the conductor with a first longitudinal section of the conductor diameter being at least partially embedded within the lead body and with a second longitudinal section of the conductor diameter that is distal of the first section and that is less embedded by the lead body than the first section, and the lead body filling the space between the first longitudinal section of the conductor and the shield. The lead also includes an electrode attached to the lead body and electrically coupled to the conductor.

DETAILED DESCRIPTION

Embodiments provide methods, medical leads, and systems where the medical leads have one or more conductors that are at least partially embedded for at least a portion of the length of the lead and where a shield is present within the lead and surrounds the conductors. Where the conductor is at least partially embedded, the lead body fills the space between the conductor and the shield so that fluids that infiltrate the lead body and reach a lumen of the lead body over time cannot pool between the conductor and the shield where the conductor is at least partially embedded.

Figure 1:
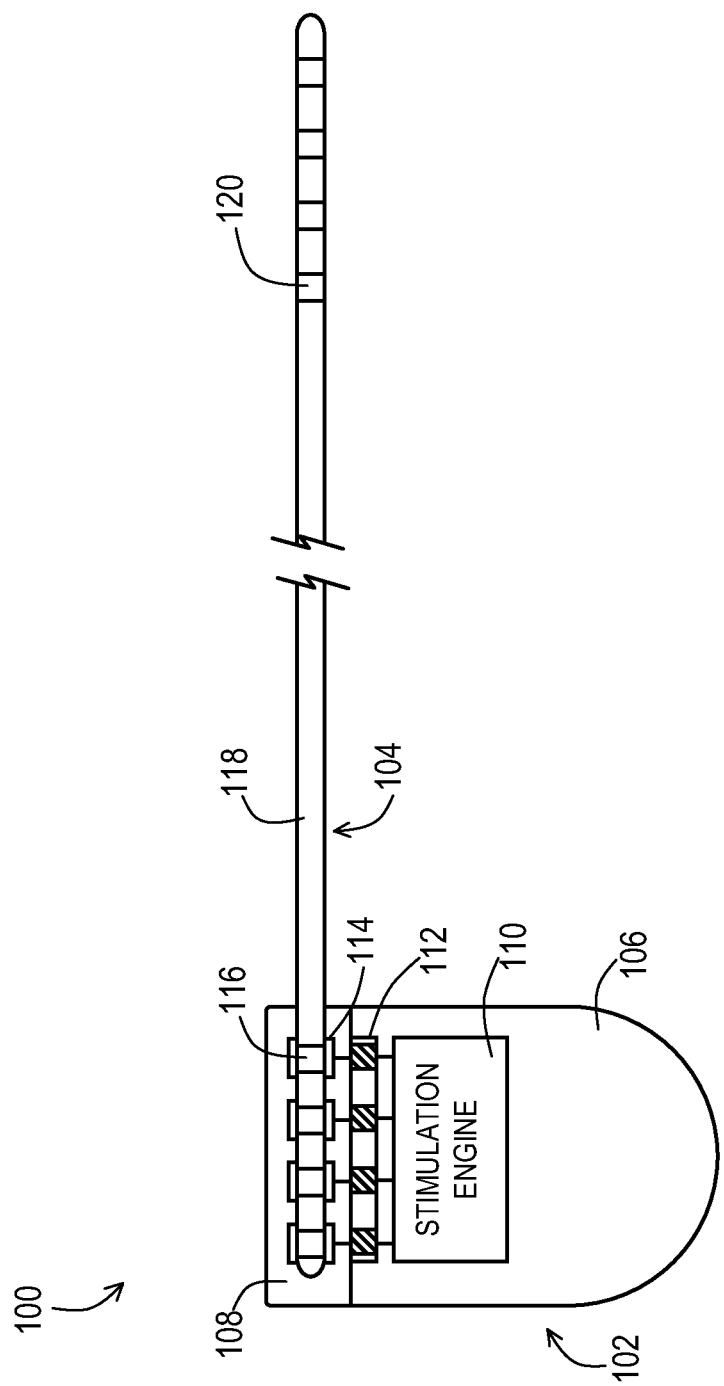
FIG. 1 shows an example of an implantable medical system that may include embodiments of the lead to reduce the coupling of the shield to the lead conductor(s).

FIG. 1 shows an example of an implantable medical system 100 that may be used to provide electrical stimulation therapy and that may reduce coupling between a shield and a conductor of a lead 104. The implantable medical system 100 includes a pulse generator 102 that includes a housing 106 that contains a stimulation engine 110 that produces the electrical stimulation signals. The pulse generator 102 may include a header 108 that includes a bore that receives a proximal end of the lead 104. The header 108 includes electrical connectors 114 that physically contact conductive contacts 116 of the lead 104. A feedthrough 114 transfers electrical signals from the sealed housing 106 to the connectors 114 of the header 104.

Figure 2A:
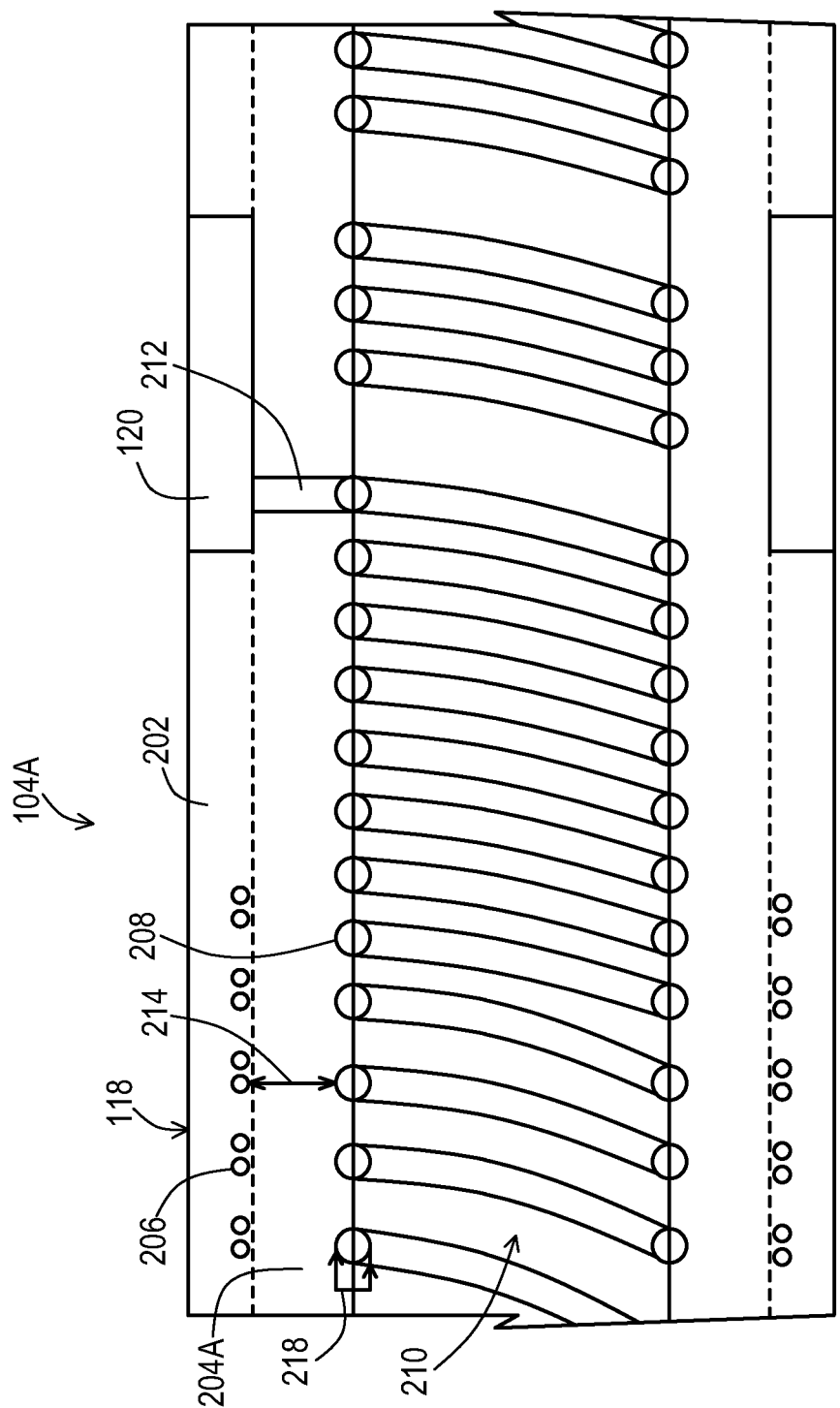
FIG. 2A shows a first example of a longitudinal cross-section of an implantable medical lead that includes a full-length partially embedded conductor to reduce the coupling of the shield to the lead conductor(s).

The lead 104 carries the electrical signals from the contacts 114 to the electrodes 120 that are coupled to the distal end of the lead body and are located at the target site within the body. FIG. 2A shows a longitudinal cross-section of a first example of the lead 104A. In this example, the lead 104A includes a collection of coiled conductors 208 that are electrically coupled to the contacts 114 of FIG. 1 and to the electrodes 120 via a radially extending portion 212. The lead 104A also includes a radio frequency (RF) shield 206 that in this example is a braid of conductive wires where the braid surrounds the conductors 208. In this example, the shield 20 is encapsulated within the lead body 118 where the lead body 118 is constructed within an insulative inner layer 204A and an insulative outer layer 202 overmolded onto the shield 206 and the inner layer 204A. Each of these layers 202, 204A may be various biocompatible and mechanically compliant materials such as polyurethane or silicone rubber. These layers 202, 204A and may have varying degrees of hardness ranging, for instance according to some embodiments the hardness may range from Shore 45A to Shore 80D.

As can be seen in this cross-section, the conductor 208 has a diameter 218 and the conductor 208 is partially embedded with a portion of the diameter 218 residing within the inner layer 204A and a portion residing within a lumen 210. In this example, one half of the diameter is embedded but it will be appreciated that the amount of the diameter 218 that is embedded may vary from one application to another. The conductor 208 in this example is partially embedded over the entire length of the conductor 208 from the proximal end at the contact 114 to the distal end at the electrode 114, which provides a high degree of isolation of the conductors 208 from the shield 206. A space 214 exists between the shield 206 and the conductors 208, and the inner layer 204A entirely fills the space 214 such that body fluids cannot pool between the conductors 208 and the shield 206. The coupling of the shield 206 to the conductor 208 is inhibited to avoid unwanted currents being channeled from the shield 206 to the conductors 208.

Figure 2B:
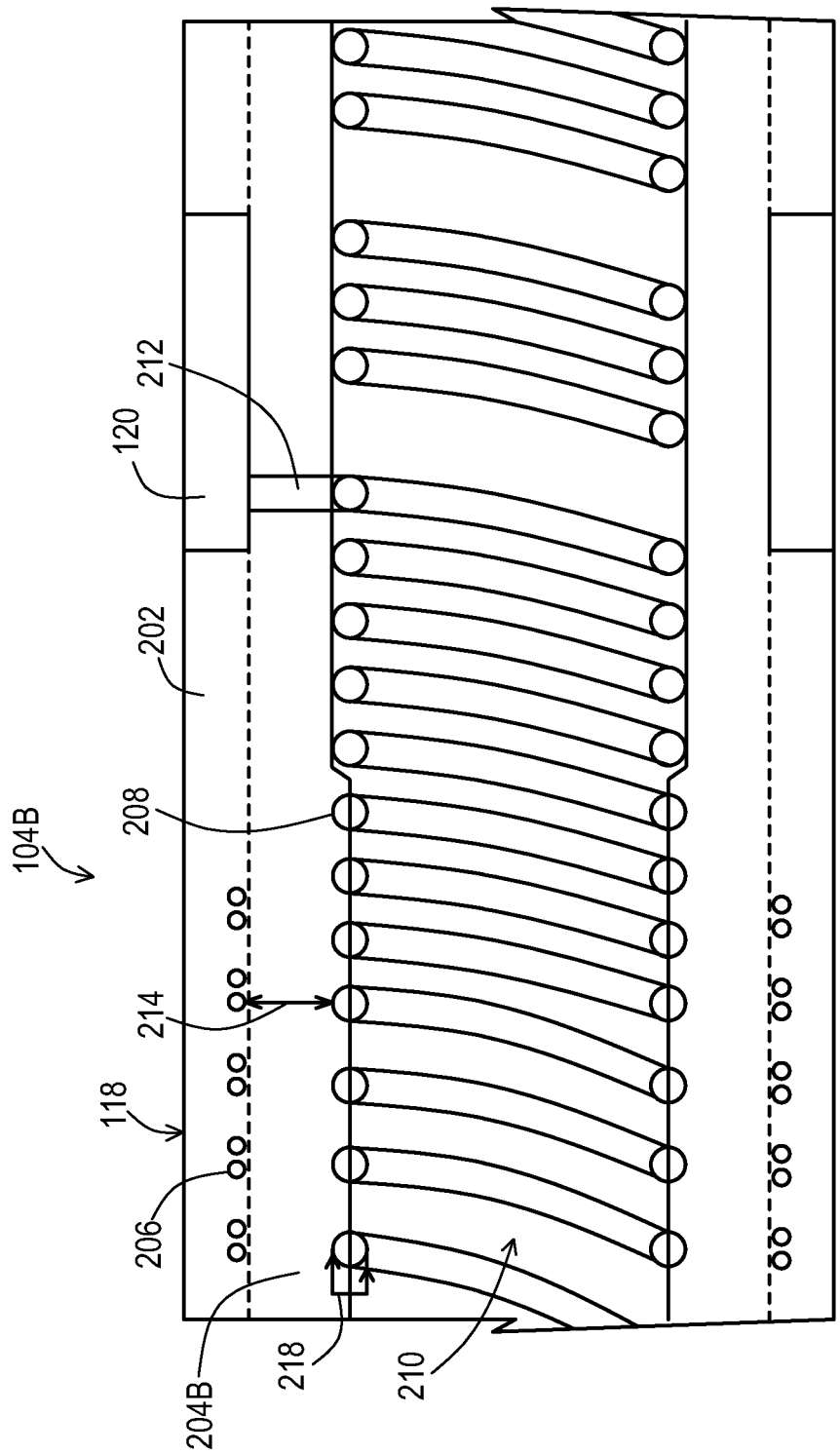
FIG. 2B shows a second example of a longitudinal cross-section of an implantable medical lead that includes a partial-length partially embedded conductor to reduce the coupling of the shield to the lead conductor(s).

FIG. 2B shows another example of a lead 104B. In this example, a first longitudinal section of the conductor 208 is partially embedded into the inner layer 204B of the lead body 118, such as one half of the diameter 218 being embedded as shown. However, the conductors 208 are not embedded to this degree over the full length and become less embedded, including being completely unembedded as shown, at a second longitudinal section in an area between a termination of the shield 206 and the proximal edge of the distal electrode 120. The conductor 208 may be less embedded by the inside diameter of the inner layer 204 increasing in size as shown, or by the outer diameter of the coil of the conductor 208 shrinking in size. This configuration continues to isolate the conductors 208 from the shield 206 to a high degree as the conductor 208 remains embedded in layer 204B for some distance beyond the shield termination but provides greater mechanical compliance of the conductors 208 near the electrodes 120 which may be beneficial in some situations.

Figure 2C:
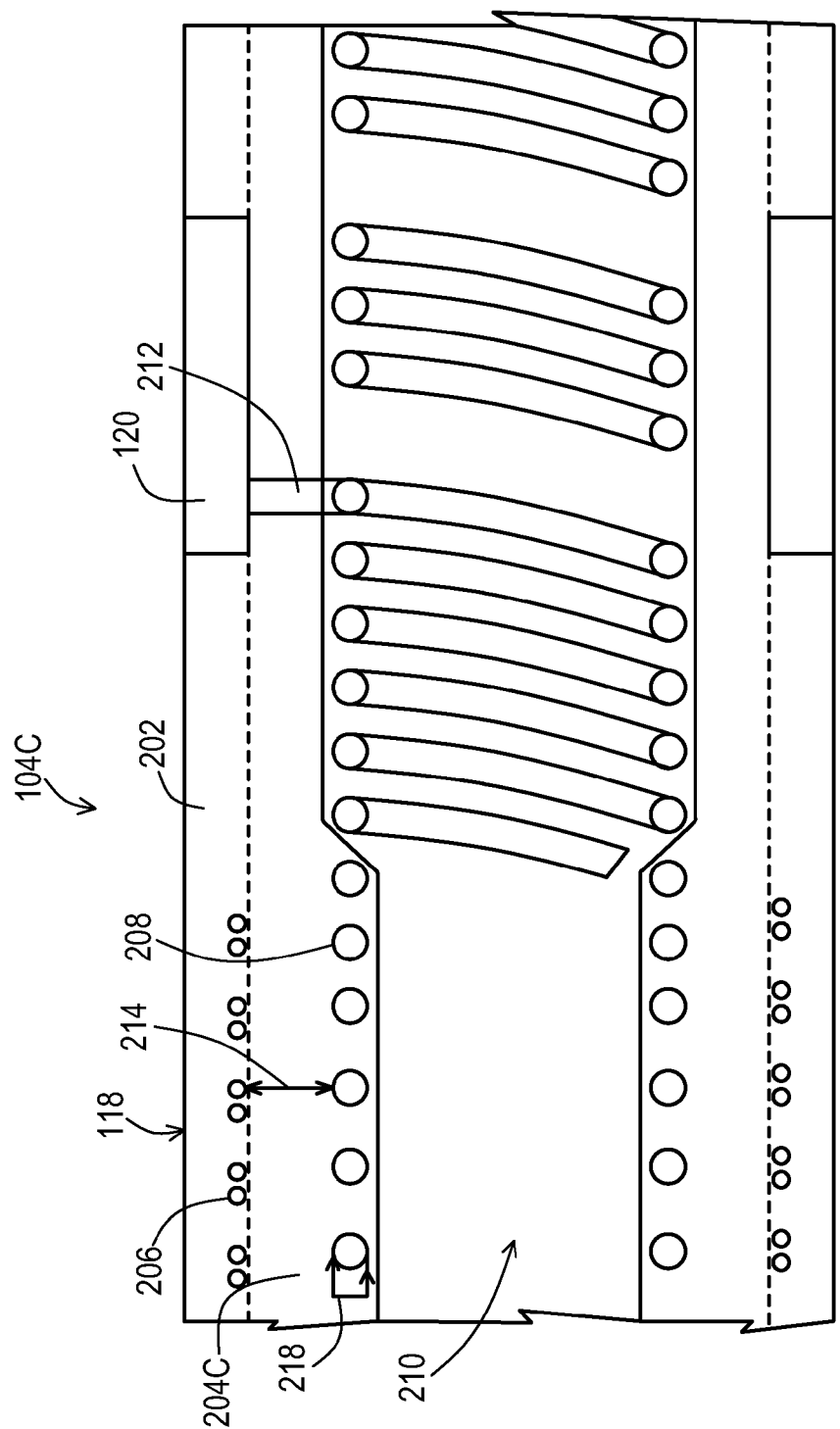
FIG. 2C shows a third example of a longitudinal cross-section of an implantable medical lead that includes a partial-length fully embedded conductor to reduce the coupling of the shield to the lead conductor(s).

FIG. 2C shows another example of a lead 104C. In this example, a first longitudinal section of the conductor 208 is fully embedded into the inner layer 204C of the lead body 118 with the full diameter 218 being present within the inner layer 204C. However, the conductors 208 are not embedded to this degree over the full length and become less embedded, including being completely unembedded as shown, at a second longitudinal section in an area between a termination of the shield 206 and the proximal edge of the distal electrode 120. This configuration continues to isolate the conductors 208 from the shield 206 to a high degree while providing increased stiffness relative to a partially embedded state as in FIG. 2B. However, like the example in FIG. 2B, the lesser embedded portion provides greater mechanical compliance of the conductors 208 near the electrodes 120 which may be beneficial in some situations.

Figure 2D:
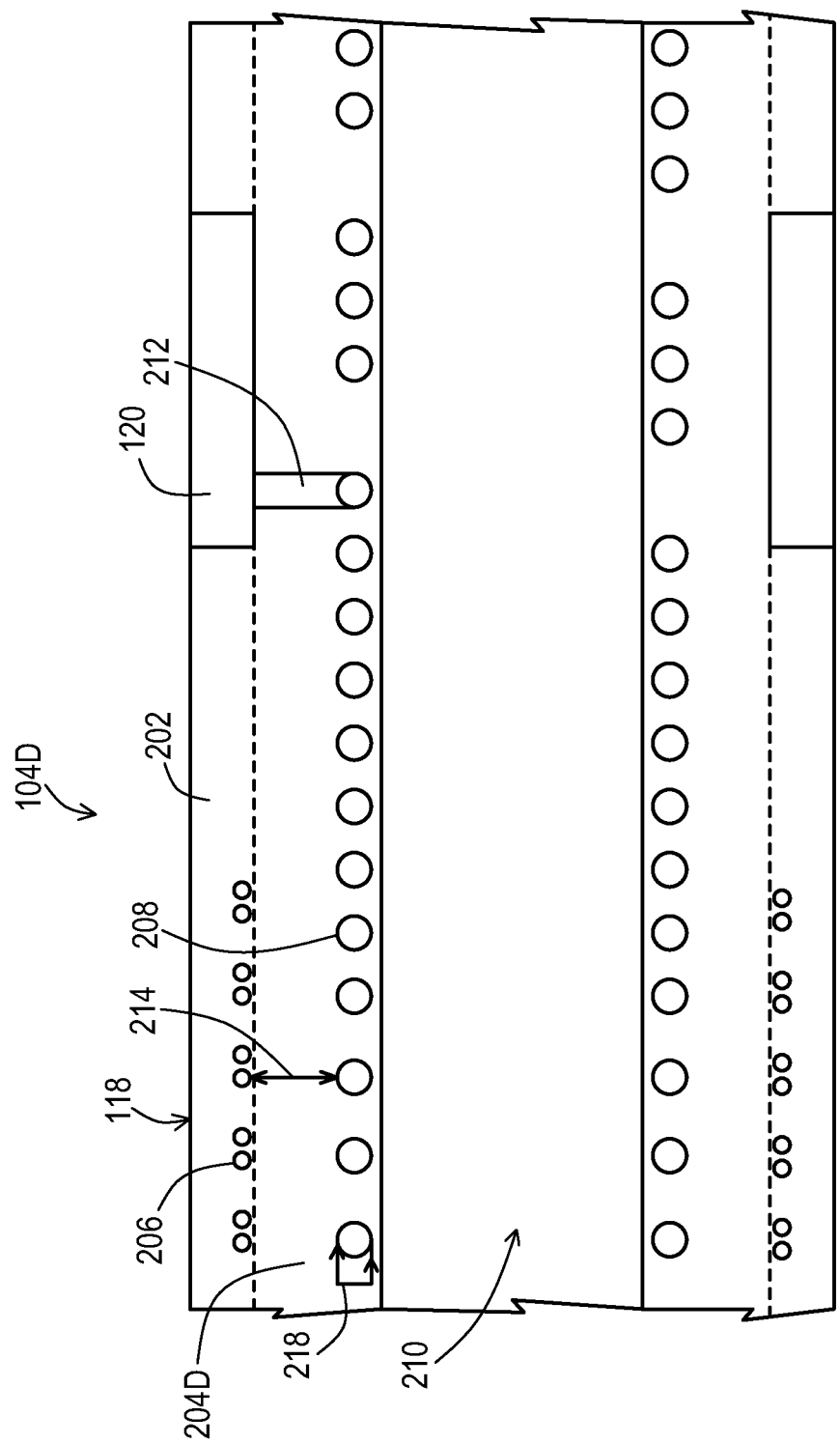
FIG. 2D shows a fourth example of a longitudinal cross-section of an implantable medical lead that includes a full-length fully embedded conductor to reduce the coupling of the shield to the lead conductor(s).

FIG. 2D shows another example of a lead 104D. In this example, the conductor 208 is fully embedded into the inner layer 204C of the lead body 118 with the full diameter 218 being present within the inner layer 204C. In this case, the conductors 208 are fully embedded over the full length from the contact 114 to the electrode 120. This configuration continues to isolate the conductors 208 from the shield 206 to a high degree while providing increased stiffness relative to a partially embedded state as in FIG. 2C and additionally stiffness at the electrodes 214 as well, which may be beneficial in some situations.

Figure 2E:
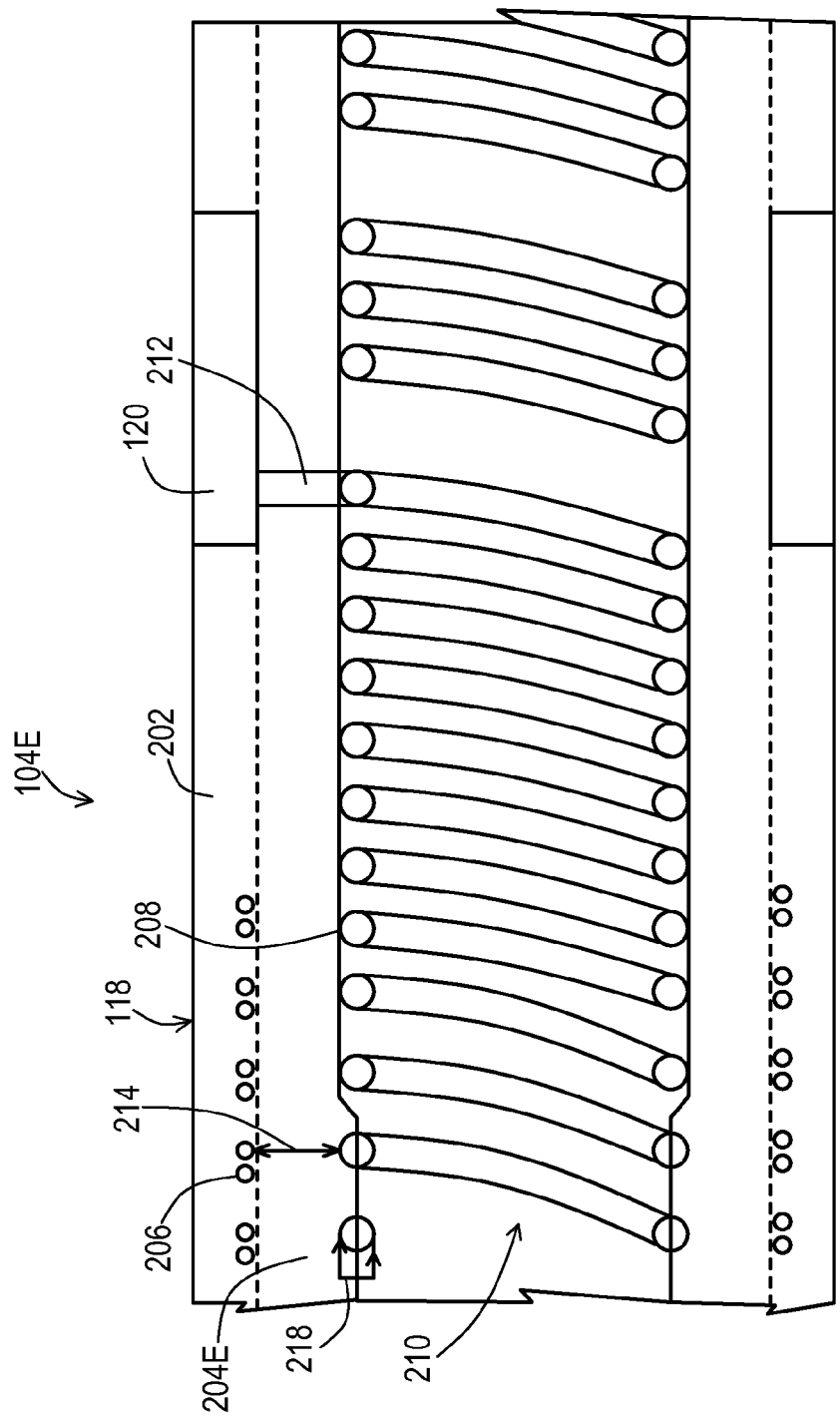
FIG. 2E shows a fifth example of a longitudinal cross-section of an implantable medical lead that includes a partial-length embedded conductor to reduce the coupling of the shield to the lead conductor(s) while providing increased conductor compliance near the electrode.

FIG. 2E shows another example of a lead 104E. In this example, a first longitudinal section of the conductor 208 is partially embedded into the inner layer 204E of the lead body 118, such as one half of the diameter 218 being embedded as shown or could also be fully embedded. However, the conductors 208 are not embedded to this degree over the full length and become less embedded, including being completely unembedded as shown, at a second longitudinal section prior to a termination of the shield 206. This configuration continues to isolate the conductors 208 from the shield 206 over a significant length of the conductor 208 but provides significantly greater mechanical compliance of the conductors 208 near the electrodes 120 where this larger degree of mechanical compliance near the electrodes 120 may be beneficial in some situations.

Figure 3:
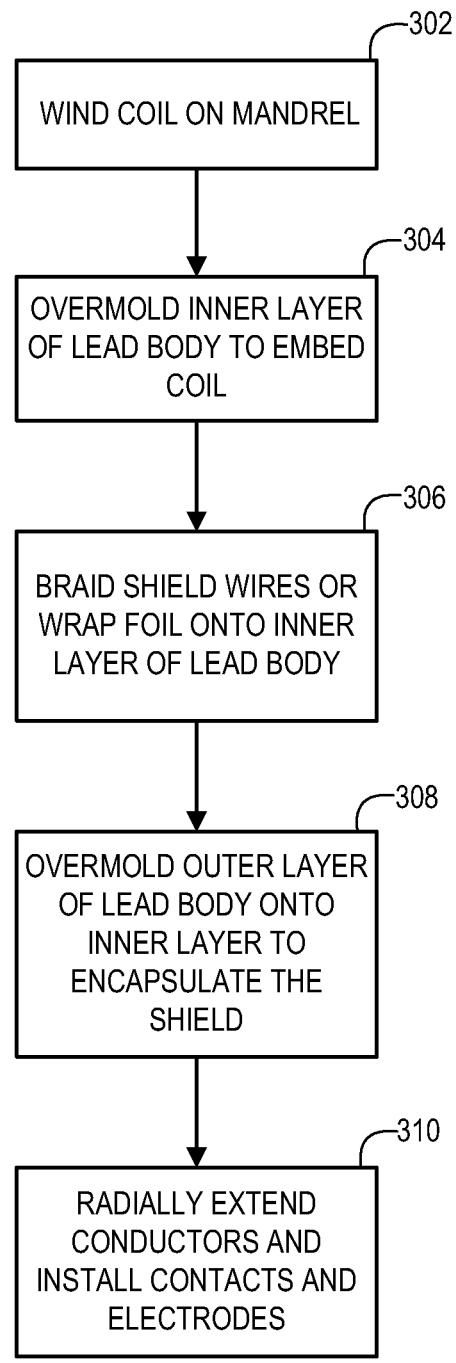
FIG. 3 shows an example of a set of operations to construct an implantable medical lead with a conductor that is at least partially embedded according to the embodiments of FIGS. 2A-2D.

FIG. 3 shows one example of a set of operations used to construct the embodiments of the lead 104. In this example, the conductors 208 are coiled and therefore straight wires are coiled around a mandrel at a coiling operation 302 to form the coiled conductors 208. The conductors may be coiled at the desired pitch and spacing as is typical for coiled conductors in medical leads. An inner layer 204 of the insulative lead body 118 is then overmolded onto the coiled conductors 208 at a molding operation 304. The overmolding may occur while the coiled conductors 208 remain on the coiling mandrel or the coiled conductors 208 may first be removed from the coiling mandrel and placed on a molding mandrel such as a stainless steel pin or wire that is coated with a polytetrafluoroethylene (PTFE) such as the Teflon® polymer from the DuPont Corporation. This overmolding operation 304 dictates the degree to which the diameter 214 of the conductors 208 is embedded into the inner layer 204. This overmolding operation 304 also dictates the length of the conductors 208 that become embedded. The overmolding operation 304 may be performed by using a heat shrink tubing as at least a portion of the inner layer 204 that contacts the conductors 208. The depth to which the diameter of the conductors 208 is present within the heat shrink tubing is controlled by the amount of shrink resulting from the chosen time and temperature of the heat shrink process. In that case, the longitudinal length of the conductors 208 that are at least partially embedded into the layer 204 is controlled by the length of the heat shrink tubing being applied to the conductors 208.

At this point, the lead assembly is ready for application of the shield 206, which may be created by braiding wires onto the inner layer 204 of the lead body 118 at a shielding operation 306. As an alternative, a conductive foil may be wrapped around the inner layer 204 at the shielding operation 306 to provide the shielding. The outer layer 202 of the lead body 118 is then overmolded atop the shielding 206 at a molding operation 308 in order to encapsulate the shield within the lead body 118. The construction of the lead 104 is completed at a conductor operation 310 by radially extending the conductor portion 212 to the position for the contact 116 on the proximal end and to the position for the electrode 120 on the distal end. The contact 116 and the electrode 120 are installed onto their respective positions on the lead body 118 with a weld or other conductive bond of the conductors 208 to the corresponding contacts 116 and electrodes 120. Other methods of manufacture may also be done, such as extruding the polymer layer over the coil while present on the mandrel, although the starting and stopping points along the length of the coil where the coil is being embedded may be less precise than where a heat shrink with a specified length is being used to achieve the embedding.

As discussed above, cabled conductors may be used in place of coiled conductors and in such a case, the cabled conductors may be positioned at their designated circumferential positions on a molding pin. Then the cabled conductors are overmolded with the inner layer 204 at the molding operation 304 and the process of FIG. 3 continues.

While embodiments have been particularly shown and described, it will be understood by those skilled in the art that various other changes in the form and details may be made therein without departing from the spirit and scope of the invention.

What is claimed is:

1. A method of providing a medical lead, comprising:
   providing a conductor having a diameter;
   providing a radio frequency (RF) shield that surrounds the conductor such that a space exists between the shield and the conductor;
   providing a lead body with a lumen, the lead body encapsulating the shield and surrounding the conductor with a portion of the conductor diameter being embedded within the lead body such that a first portion of the conductor diameter is present within the lumen and a second portion of the conductor diameter is sunken into a lumen wall forming the lumen, and the lead body filling the space; and
   providing an electrode attached to the lead body and electrically coupled to the conductor.

2. The method of claim 1, wherein the conductor is coiled.

3. The method of claim 1, wherein the shield comprises wires.

4. The method of claim 3, wherein half of the diameter of the conductor is embedded within the lead body and half of the diameter of the conductor is present within the lumen.

5. The method of claim 1, wherein the shield terminates prior to the location of the electrode and the portion of the diameter of the conductor is embedded within the lead body in an area of the lead body between the termination of the shield and the electrode.

6. A method of providing a medical lead, comprising:
   forming an inner lead body layer of a lead body about a conductor to embed a first lengthwise portion of the conductor within the inner lead body layer such that the first lengthwise portion of the conductor is at least partially sunken into a lumen wall forming the lumen while a second lengthwise portion of the conductor resides in the lumen and is surrounded by the lumen wall;
   positioning a radio frequency (RF) shield about the lead body inner layer;
   forming an outer lead body layer of the lead body about the shield and the inner lead body layer to encapsulate the shield and to bond with the inner lead body layer; and
   providing an electrode attached to the lead body and electrically coupled to the conductor.

7. The method of claim 6, wherein the conductor is coiled.

8. The method of claim 6, wherein the shield comprises wires.

9. The method of claim 8, wherein the shield comprises braided wires.

10. The method of claim 6, wherein the shield terminates prior to the location of the electrode and the first lengthwise portion of the conductor is embedded within the inner lead body layer in an area of the lead body between the termination of the shield and the electrode.

11. An implantable medical lead, comprising:
    a conductor having a diameter;
    a radio frequency (RF) shield that surrounds the conductor such that a space exists between the shield and the conductor;

a lead body with a lumen, the lead body encapsulating the shield and surrounding the conductor with a portion of the conductor diameter being embedded within the lead body such that a first portion of the conductor diameter is present within the lumen and a second portion of the conductor diameter is sunken into a lumen wall forming the lumen, and the lead body filling the space; and an electrode attached to the lead body and electrically coupled to the conductor.

12. The lead of claim 11, wherein the conductor is coiled.

13. The lead of claim 11, wherein the shield comprises wires.

14. The lead of claim 13, wherein half of the diameter of the conductor is embedded within the lead body and half of the diameter of the conductor is present within the lumen.

15. The lead of claim 11, wherein the shield terminates prior to the location of the electrode and the portion of the diameter of the conductor is embedded within the lead body in an area of the lead body between the termination of the shield and the electrode.

16. An implantable medical system, comprising:
a pulse generator; and
a medical lead, comprising:
 a conductor having a diameter, the conductor being electrically coupled to the pulse generator;
 a radio frequency (RF) shield that surrounds the conductor such that a space exists between the shield and the conductor;
 a lead body with a lumen, the lead body encapsulating the shield and surrounding the conductor with a portion of the conductor diameter being embedded within the lead body such that a first portion of the conductor diameter is present within the lumen and a second portion of the conductor diameter is sunken into a lumen wall forming the lumen, and the lead body filling the space; and
 an electrode attached to the lead body and electrically coupled to the conductor.

17. The system of claim 16, wherein the conductor is coiled.

18. The system of claim 16, wherein the shield comprises wires.

19. The system of claim 18, wherein half of the diameter of the conductor is embedded within the lead body and half of the diameter of the conductor is present within the lumen.

20. The system of claim 16, wherein the shield terminates prior to the location of the electrode and the portion of the diameter of the conductor is embedded within the lead body in an area of the lead body between the termination of the shield and the electrode.

21. An implantable medical lead, comprising:
a conductor having a diameter;
a radio frequency (RF) shield that surrounds the conductor such that a space exists between the shield and the conductor;
a lead body with a lumen, the lead body encapsulating the shield and surrounding the conductor with a first longitudinal section of the conductor diameter being at least partially embedded within the lead body such that the conductor is at least partially sunken into a lumen wall forming the lumen and with a second longitudinal section of the conductor diameter that is distal of the first longitudinal section and being less embedded by the lead body than the first section, and the lead body filling the space between the first section of the conductor and the shield; and
an electrode attached to the lead body and electrically coupled to the conductor.

\* \* \* \* \*